(12) United States Patent
Hintzer et al.

(10) Patent No.: US 6,482,979 B1
(45) Date of Patent: Nov. 19, 2002

(54) PERFLUORINATED ACID FLUORIDES AND PREPARATION THEREOF

(75) Inventors: Klaus Hintzer, Woodbury, MN (US); Zai-Ming Qiu, Woodbury, MN (US); George G. I. Moore, Afton, MN (US); Werner Schwertfeger, Bavaria (DE); Jay F. Schulz, Eagan, MN (US); Allan T. Worm, North St. Paul, MN (US); Christopher L. Gross, Woodbury, MN (US)

(73) Assignees: Dyneon LLC, Oakdale, MN (US); 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/470,035

(22) Filed: Dec. 22, 1999

(51) Int. Cl.$^7$ .......................... C07C 59/00; C07C 69/66
(52) U.S. Cl. ..................... 562/586; 560/184; 423/481; 423/483
(58) Field of Search .......................... 562/586; 560/184; 423/481, 483

(56) References Cited

U.S. PATENT DOCUMENTS

| | | | |
|---|---|---|---|
| 2,713,593 A | * | 7/1955 | Brice et al. |
| 2,988,537 A | * | 6/1961 | Wiley et al. |
| 3,274,081 A | | 9/1966 | Pearlson ...................... 204/59 |
| 4,273,728 A | | 6/1981 | Krespan ................... 260/465.6 |
| 4,281,119 A | * | 7/1981 | Lagow et al. |
| 4,418,186 A | | 11/1983 | Yamabe et al. .............. 526/247 |
| 4,523,039 A | | 6/1985 | Lagow et al. ................ 568/615 |
| 4,599,386 A | | 7/1986 | Carlson et al. ........... 525/326.2 |
| 4,686,024 A | | 8/1987 | Scherer, Jr. et al. .... 204/157.95 |
| 4,774,304 A | | 9/1988 | Kuhls et al. ................. 526/247 |
| 4,859,747 A | | 8/1989 | Bierschenk et al. ........ 525/409 |
| 4,931,511 A | | 6/1990 | Kawachi et al. ......... 525/326.3 |
| 4,960,951 A | | 10/1990 | Nappa ........................ 568/615 |
| 5,093,432 A | * | 3/1992 | Bierschenk et al. |
| 5,115,038 A | | 5/1992 | Ihara et al. ............... 525/326.2 |
| 5,235,094 A | | 8/1993 | Darst et al. ................. 560/184 |
| 5,318,674 A | | 6/1994 | Behr et al. ................. 204/59 F |
| 5,362,919 A | | 11/1994 | Costello et al. ............. 568/601 |
| 5,466,877 A | | 11/1995 | Moore ........................ 562/852 |
| 5,488,142 A | * | 1/1996 | Fall et al. |
| 5,639,838 A | | 6/1997 | Albano et al. ............... 526/247 |
| 5,696,616 A | | 12/1997 | Wagensonner ............... 359/201 |
| 5,891,965 A | | 4/1999 | Worm et al. .............. 525/326.3 |
| 5,891,974 A | | 4/1999 | Saito et al. .................. 526/247 |

FOREIGN PATENT DOCUMENTS

| | | | |
|---|---|---|---|
| EP | 0 055 407 | 7/1982 | ......... C08F/214/22 |
| EP | 0 148 482 | 7/1985 | ........... C08G/65/22 |
| EP | 0 290 848 | 11/1988 | ........... C07C/43/17 |
| EP | 0 354 420 A | 2/1990 | ........... C07C/51/58 |
| JP | 59177384 A | 8/1984 | ............. C25B/3/08 |
| WO | WO 98/50603 | 11/1998 | ............. C25B/3/08 |

OTHER PUBLICATIONS

Berenblit V. V. et al, Electrochemical Fluorination of Alkoxycarboxylates, Zh. Prikl. Khim., 1975, vol. 48 (30, 709–711.*
Chemical Abstracts, vol. 83, No. 23, Dec. 8, 1975, Columbus, Ohio, US; abstract No. 192495y, Adcock, J.L. et al, "Successful Direct Fluorination of Oxygen–Containing Hydrocarbons", p. 389, col. 2, & J. Org. Chem., vol. 40, No. 22, 1975, pp. 3271–3275, Abstract.
"Modern Fluoropolymers", John Scheirs, Wiley Series in Polymer Science, 1997.
Emel'yanov et al, Zh. Org. Khim, (1994) 30(8), pp. 1266–1270.
V. V. Berenblit et al, Zh. Prikl, Khim. (Leningrad), (1975) 48(3) pp. 709–711.
Kirk Othmer Encyclopedia of Chemical Technology, $3^{rd}$ Edition, vol. 10, pp. 636, 840–855, John Wiley & Sons, Inc., New York, NY (1980).
Lagow et al., "Progress in Inorganic Chemistry", vol. 26, pp. 161–210 (1979).
"Electrofluorination of Organic Compounds", Fred G. Drakesmith, pp. 197–242, Topics In Current Chemistry, vol. 193, ©Springer Verlag Berlin Heidelberg 1997.
Journal of Fluorine Chemistry, vol. 27, 1985, pp. 333–346.

* cited by examiner

Primary Examiner—Alan L. Rotman
Assistant Examiner—Hector M Reyes
(74) Attorney, Agent, or Firm—James V. Lilly; Brian E. Szymanski

(57) ABSTRACT

A method for the preparation of a perfluorinated acid fluoride (especially 3-alkoxy propionic acid fluoride) is provided. The method results in high yields of the acid fluoride.

22 Claims, No Drawings

PERFLUORINATED ACID FLUORIDES AND PREPARATION THEREOF

FIELD OF THE INVENTION

The present invention is related to perfluorinated acid fluorides, especially perfluorinated 3-alkoxy propionic acid fluorides, and a method of preparing such compounds. These compounds are valuable intermediates for e.g. vinyl ethers that can be used to prepare a variety of fluoropolymers including those having enhanced low temperature properties.

BACKGROUND OF THE INVENTION

Fluorinated vinyl ethers have found applicability in numerous fluoropolymers. For example, they may be copolymerized with tetrafluoroethylene (TFE) to produce modified polytetrafluoroethylene (mPTFE). Likewise, they may be copolymerized with a variety of other fluorinated monomers to produce fluoroplastic and/or fluoroelastomeric polymers. Some of the benefits of employing vinyl ethers in fluoropolymers are described in various review articles. See for example, Modern Fluoropolymers, John Scheirs, Wiley Series in Polymer Science, 1997. See also Emel'yanov et al, Zh. Org. Khim (1994), 30(8), 1266–70.

There are a number of routes to prepare fluorinated vinyl ethers. Generally these routes start with perfluorinated acid fluorides. See for example Modern Fluoropolymers, J. Scheirs, Wiley Series in Polymer Science, 1997 and the literature cited therein.

Even though perfluorinated acid fluorides are commonly used in the synthesis of fluorinated vinyl ethers, there are only a few synthetic routes that are known to lead to perfluorinated 3-alkoxy propionic fluorides starting from hydrogen containing precursors.

For example, U.S. Pat. No. 2,713,593 discloses the electrochemical fluorination of a nonfluorinated carboxylic acid chloride to form perfluorinated acid fluoride.

Another synthesis route is disclosed in V. V. Berenblit et al., Zh, Prikl. Khim. (Leningrad), (1975) 48(3) 709–11. In this route a hydrocarbon ester is electrochemically fluorinated to provide the perfluorinated acid fluoride.

These synthesis routes are not entirely satisfactory because yield of acid fluoride is low, e.g., less than 15% by weight. This is in keeping with the generally low yields of ethers during electrochemical fluorination.

A third route to the synthesis of acid fluorides is disclosed in EPA 148,482 (Ohsaka et al) and EPA 290,848 (Oka et al). In this route, tetrafluorooxetane is reacted with an at least partially fluorinated acid fluoride. The resulting intermediate is fluorinated to provide a perfluorinated acid fluoride. This synthesis route has at least two disadvantages. First, the tetrafluorooxetane must be synthesized. This adds additional steps, time and cost to the synthesis of the acid fluoride. Second, the reaction of the at least partially fluorinated acid fluoride with the oxetane may result in the formation of oligomers thereby reducing the yield of the desired acid fluoride.

SUMMARY OF THE INVENTION

The present invention provides a process for the preparation of a perfluorinated acid fluoride from a partially fluorinated, hydrogen-containing starting material. The process of the present invention provides a perfluorinated acid fluoride has the formula $$R_fOCF_2CF_2COF \qquad (1)$$

wherein $R_f$ is a perfluorinated linear or branched monovalent aliphatic, preferably alkyl, radical that has from 1–20 (preferably from 1 to 5) carbon atoms. The method of the invention comprises the steps of (a) providing a partially fluorinated, hydrogen-containing starting material of the formula $$ROCF_2CF_2COZ \qquad (2).$$

wherein R is a monovalent, hydrogen-containing, linear or branched aliphatic (preferably alkyl) radical that may contain oxygen atoms and that contains from 1–20 (preferably from 1 to 5) carbon atoms; and Z is selected from —OH, a halogen (e.g., chlorine or fluorine) or a monovalent hydrogen-containing linear or branched alkyl or alkoxy group that contains 1–20 (preferably 1–5) carbon atoms, or an anhydride radical selected from R'COO— where R' is selected from R or ROCF$_2$CF$_2$COO— where R is as defined above;

(b) fluorinating the starting material by contacting it with a fluorinating agent under conditions sufficient to replace hydrogen atoms on the starting material with fluorine; and (c) optionally converting the product of step (b) to the perfluorinated acid fluoride.

R and Z may be partially fluorinated if desired. Additionally, R and Z may contain one or more oxygen atoms.

As it is used herein, the term perfluorinated means that all of the carbon-bonded hydrogen atoms have been replaced by fluorine.

Surprisingly, the process of the invention provides high yields (preferably 50 mole % or more) of the perfluorinated acid fluoride of the Formula (1). Prior art techniques for producing acid fluorides of formula (1) typically result in yields of the acid fluoride of substantially less than 50 mole %, typically less than 25 mole %. Additionally, the process of the invention is simple to use. It provides the desired acid fluoride in a straight forward manner.

DETAILED DESCRIPTION

The starting material for the process of the invention is the hydrogen-containing compound of the formula $$ROCF_2CF_2COZ \qquad (2)$$

wherein R and Z are as described above. R and Z may be the same or different from one another. Preferably at least one of R and Z is a methyl or ethyl group. The starting materials of Formula (2) are preferably esters, anhydrides or ketones.

When the starting material for the process of the invention is an ester or an anhydride, it has the formula $$ROCF_2CF_2COOR'' \qquad (3)$$

wherein R" is a monovalent, hydrogen containing alkyl radical that contains from 1 to 20 (preferably 1 to 5) carbon atoms or

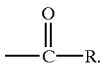

When the starting material is a ketone, it preferably has the formula $$ROCF_2CF_2COCF_2CF_2OR \qquad (4)$$

where R is as described above.

Starting materials useful in the invention have been previously described. See, for example, U.S. Pat. No. 2,988,537 (Wiley), which disclose the reaction of tetrafluoroethylene (TFE) with a sodium alkoxylate in the presence of a dialkyl carbonate. This reaction forms a compound which may then be treated with anhydrous acid to yield a hydrogen-containing, partially fluorinated starting material of Formula (2). This reaction sequence may be graphically represented by the following:

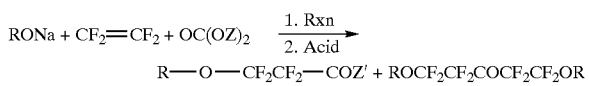

wherein Z' is selected from a halogen, or a monovalent hydrogen containing linear or branched alkyl group of from 1 to 20 carbon atoms, and R is as defined above.

See also U.S. Pat. No. 5,235,094 (Darst et al) which discloses another route to the synthesis of a partially fluorinated ester of Formula (3).

The partially fluorinated esters of Formula (3) can be transformed to corresponding anhydrides using procedures well-known to those skilled in the art.

The partially fluorinated starting material is fluorinated by contacting it with fluorine to form an intermediate in which all of the hydrogen atoms present on the starting material are replaced with fluorine. This is done under conditions that are appropriate to replace the hydrogen on the starting material, but not so aggressive that backbone of the starting material is disturbed.

Fluorination of the starting material can be accomplished by a number of techniques. Examples of useful fluorination techniques include electrochemical fluorination (ECF) and direct fluorination (DF).

Electrochemical fluorination is a well known technique that is disclosed in a number of publications including U.S. Pat. No. 2,713,593 and WO 98/50603. It is a process that employs hydrogen fluoride. Electrochemical fluorination of the starting material results directly in the desired perfluorinated acid fluoride of Formula (1). As a result, there is no need to convert the product of this step any further. Surprisingly, the use of the partially fluorinated precursor of Formula (2) as the starting material results in unexpectedly high yields of the acid fluoride.

Direct fluorination is another well known technique. This technique is disclosed in a host of articles and patents. See for example, U.S. Pat. No. 5,488,142 (Fall et al); U.S. Pat. No. 4,523,039 (Lagow et al); Kirk Othmer Encyclopedia of Chemical Technology, 3$^{rd}$ Edition, V. 10, pp 636, 840–855, John Wiley & Sons, Inc., New York, N.Y. (1980); Lagow et al, Progress in Inorganic Chemistry, 26, 161–210 (1979); U.S. Pat. No. 4,859,747 (Bierschenk et al).

During direct fluorination, fluorine, which may be diluted with an inert liquid or gas, and the starting material are contacted in an appropriate vessel (e.g., either a stirred tank reactor or a tubular reactor). The amounts of each are selected to have a stoichiometric excess of fluorine. Fluorination is allowed to take place for a time sufficient to replace all of the hydrogens on the precursor with fluorine.

Direct fluorination of a partially fluorinated starting material is preferably carried out in the presence of an unfluorinated coreactant. The coreactant is often selected from certain common organic solvents. Preferably, the coreactant provides a source of reactive hydrogen that initiates free radical chain reactions between the starting material and a the fluorinating agent.

It has been discovered that with the proper selection of the unfluorinated reactant, the yield of the acid fluoride is significantly improved over that otherwise achieved in the practice of the invention. Preferred unfluorinated reactants which provide this surprising enhancement of the yield are non-chlorinated, non-hydroxylic compounds. Most preferably they are ethers. Low molecular weight materials (e.g., weight average molecular weight of 150 or less) are the most preferred.

Examples of unfluorinated reactants that are useful in the practice of the present invention include polar, aprotic compounds and nonpolar, aprotic compounds. Representative examples of polar, aprotic compounds include hydrocarbon esters, acyclic ethers such as diethyl ether, ethylene glycol dimethyl ether, and diethylene glycol dimethyl ether; cyclic ethers such as tetrahydrofuran, 2-methyltetrahydrofuran, dioxane, dioxolane, and 4-methyldioxolane; ketones such as acetone and 2-butanone; carboxylic acid esters such as methyl formate, ethyl formate, methyl acetate, diethyl carbonate, propylene carbonate, ethylene carbonate, and butyrolactones. Mixtures of polar aprotic compounds may be used if desired. Representative examples of useful nonpolar, aprotic compounds include toluene, benzene, hexane, heptane and the like. Mixtures of nonpolar, aprotic compounds may be used if desired. If desired, polar, aprotic compounds can be mixed with nonpolar, aprotic compounds. Factors involved in the selection include compatability of the unfluorinated reactants with the starting material to be fluorinated and ease of separation of perfluorinated products.

The unfluorinated coreactants and the partially fluorinated compound of Formula (2) are preferably simultaneously fed to the fluorination vessel. As little as 10% by weight of the coreactant has been found to have a beneficial effect upon yield.

Direct fluorination of the starting material results in the formation of a fluorinated intermediate which is then converted to the perfluorinated acid fluoride by techniques known to the art. For example, the intermediate can be converted to the acid fluoride as is described in U.S. Pat. No. 5,466,877 (Moore). Other techniques are, of course, also useful in this conversion.

Examples of useful nucleophiles include metal fluorides (e.g., cesium fluoride, potassium fluoride), or tertiary amines (e.g., trialkylamines, pyridine) in an aprotic polar solvent.

As with electrochemical fluorination, direct fluorination of the starting material results in unexpectedly high yields of the acid fluoride.

Examples of perfluorinated acid fluorides that may be prepared by the process of the invention include

As disclosed previously, the acid fluorides prepared by the process of the invention are useful in the preparation of perfluorinated vinyl ethers. These ethers are useful as comonomers in a variety of polymers such as those disclosed in U.S. Pat. No. 4,599,386 (Carlson et al); U.S. Pat. No. 5,115,038 (Ihara et al); U.S. Pat. No. 4,774,304 (Kuhls et al); U.S. Pat. No. 5,696,616; U.S. Pat. No. 5,639,838; U.S. Pat. No. 4,931,511; U.S. Pat. No. 4,418,186; and U.S. Pat. No. 5,891,965.

EXAMPLES

Example 1

A 1000 ml electrochemical fluorination cell similar to the type described in U.S. Pat. No. 2,713,593 (Brice et al.) was equipped with a 0.037 m² (0.40 ft²) nickel anode, one −40° C. and one −80° C. condenser, both of which convergently drained into a 0.3 L stainless steel decanter. The cell was charged with approximately 900 ml anhydrous HF maintained at 1800 torr (35 psig) and 58° C. while 2224.5 g of a mixture of 90% (wt) $CH_3OCF_2CF_2CO_2CH_3$, 5% $(CH_3OC_2F_4)_2C=O$ and 5% dimethyl disulfide was 218.9 hr. Additional HF was added during the reaction to maintain the fluid level at 900 ml.

Fluorination was carried out as described in Example 1 of WO 98/50603. The cell was operated at an average current of 19.5 amps and an average voltage of 6.0 volts. After the cell had reached steady-state, the current was periodically and regularly interrupted. The current flowed at a first current of 19.5 amps for a first time ($T_e$) of 80 seconds. The current flow was then stopped for a second time ($T_i$) of 4 seconds.

The crude liquid fluorinated product was collected periodically from the decanter, for a total of 2384.6 g. In addition, the HF phase in the decanter (total 618.3 g) was found to contain 25 mole % w/w product. The total yield of $CF_3OCF_2CF_2C(O)F$ was approximately 55 mole % of theoretical as determined by GC/IR, GC/MS and 19F/1H NMR. Additionally, the byproduct $CHF2OCF_2CF_2C(O)F$ was produced in approximately 15 mole % yield.

When this example was repeated using the hydrocarbon ester (that is it was not partially fluorinated) as the starting material, the total yield of the acid fluoride was 21 mole %.

Example 2

Using a tubular direct fluorination apparatus similar to the type described by Fall and Guerra in U.S. Pat. No. 5,488,142, 108.9 g of 90% (w/w) $CH_3OC_2F_4COOCH_3$ —10% THF was added at 10 ml/hr to a rapidly circulating batch of 5472.7 g perfluoro(N-methylmorpholine) to which a gas stream comprised of 400 ml/min $F_2$ and 1600 ml/min $N_2$ was continuously introduced. The temperature was maintained at 20° C. during the 9.3 hr reaction. Analysis of the crude product by 19F/1H NMR indicated that the yield of the perfluorinated ester was 75 mole % based on the starting material. The perfluorinated ester was converted to the acid fluoride by contacting the ester with a catalytic amount of pyridine. When this example was repeated without using the THF, the yield was 51 mole %.

When this example was repeated using the hydrocarbon ester (that is it was not partially fluorinated) as the starting material, the total yield of the acid fluoride was 31 mole %.

Example 3

A 1000 ml electrochemical fluorination cell similar to the type described in U.S. Pat. No. 2,713,593 (Brice et al.) was equipped with a 0.037 m² (0.40 ft²) nickel anode, one −40° C. and one −80° C. condenser, both of which convergently drained into a 0.3 L stainless steel decanter. The cell was charged with approximately 900 ml anhydrous HF maintained at 1800 torr (35 psig) and 58° C. while 977.9 g of a mixture of 95% (wt) $CH_3OCF_2CF_2C(O)CF_2CF_2OCH_3$ and 5% dimethyl disulfide was added over 93.0 hr. Additional HF was added during the reaction to maintain the fluid level at 900 ml.

Fluorination was carried out as described in WO 98/50603 using procedures similar to those of Example 1. The cell was operated at an average current of 19.5 amps and an average voltage of 6.1 volts. After the cell had reached steady-state, the current was periodically and regularly interrupted. The current flowed at a first current of 17.8 amps for a first time ($T_e$) of 80 seconds. The current flow was then stopped for a second time ($T_i$) of 4 seconds.

The crude liquid fluorinated product was collected periodically form the decanter, for a total of 1269.9 g. In addition, the HF phase in the decanter (total 364.1 g) was found to contain 2 mole % w/w product. The total yield of $CF_3OCF_2CF_2C(O)F$ was approximately 50 mole % of theoretical as determined by GC/IR, GC/MS and 19F/1H NMR.

Example 4

The partially fluorinated anhydride $(CH_3OC_2F_4CO)_2O$ was prepared from $CH_3OC_2F_4COOCH_3$. The ester (83 g, 0.438 mol) $CH_3OC_2F_4COOCH_3$ was titrated with aqueous NaOH and MeOH was removed. Concentrated aqueous HCl was added to give 68 g $CH_3OC_2F_4COOH$, bp 76–78° C./15 mm for an 88% yield. A sample of 48 g sample $CH_3OC_2F_4COOH$ was dehydrated with $P2O_5$ to give 36 g $(CH_3OC_2F_4CO)_2O$, bp 72–76° C./15 mm. The resulting partially fluorinated compound was then directly fluorinated using a tubular direct fluorination apparatus similar to the type described by Fall and Guerrain U.S. Pat. No. 5,488,142. Direct fluorination of 19.6 g of $(CH_3OC_2F_4CO)_2O$ in perfluoro(N-methylmorpholine) at 25° C. with 10% THF as a cosolvent gave 14.5 g $(CF_3OC_2F_4CO)_2O$ identified by 19F NMR in a 56% yield. The perfluorinated anhydride can be converted to the acid fluoride using known techniques. For example, it can be reacted with KF to form a mixture of the acid fluoride and the corresponding potassium salt. The salt can then be converted to the acid fluoride in a subsequent reaction. Alternatively, the anhydride can be reacted with HF to provide the acid fluoride by contacting the anhydride with a catalytic amount of pyridine.

What is claimed is:

1. A method of making a perfluorinated acid fluoride having the formula $$R_fOCF_2CF_2COF \qquad (1)$$

wherein $R_f$ is a perfluoroaliphatic group having from 1 to 20 carbon atoms, comprising the steps of (a) providing a partially fluorinated, hydrogen-containing starting material of the formula selected from $$R—O—CF_2CF_2COZ \qquad (2)$$

wherein R is a monovalent hydrogen-containing aliphatic group that may contain one or more oxygen atoms and that has from 1 to 20 carbon atoms and Z is selected from —OH, a halogen, a monovalent, hydrogen-containing linear or branched alkyl or alkoxy group from 1 to 20 carbon atoms, and an acyloxy radical selected from RCOO— or $ROCF_2CF_2COO$—; and (b) fluorinating the starting material by contacting the starting material with a fluorinating agent under conditions sufficient to replace the hydrogen atoms on the starting material with fluorine; and (c) optionally converting the product of step b) to the perfluorinated acid fluoride.

2. The method of claim 1 wherein at least one of R and Z are partially fluorinated.

3. The method of claim 1 wherein R and Z are free from fluorine.

4. The method of claim 1 wherein each R and Z independently have from 1 to 5 carbon atoms.

5. The method of claim 1 wherein at least one of R contains a methyl or ethyl group and Z contains a methoxy or an ethoxy group.

6. The method of claim 1 wherein Z is a halogen.

7. The method of claim 1 wherein step (b) is done by electrochemical fluorination.

8. The method of claim 1 wherein step (b) is done by direct fluorination.

9. The method of claim 1 wherein the starting material has the formula $$R—O—CF_2CF_2COOR'' \qquad (3)$$

wherein R" is a monovalent, hydrogen containing alkyl radical that contains from 1 to 20 carbon atoms and R is as defined in claim 1.

10. The method of claim 9 wherein R and R" are partially fluorinated.

11. The method of claim 9 wherein R and R" are free from fluorine.

12. The method of claim 9 wherein each R and R" independently have from 1 to 5 carbon atoms.

13. The method of claim 9 wherein at least one of R and R" is methyl or ethyl.

14. The method of claim 9 wherein R is an alkyl group.

15. The method of claim 1 wherein the starting material has the formula $$ROCF_2CF_2COCF_2CF_2OR \qquad (4)$$

wherein R is a linear or branched, hydrogen-containing aliphatic group having from 1 to 20 carbon atoms.

16. A method of making a perfluorinated acid fluoride having the formula $$R_fOCF_2CF_2COF \qquad (1)$$

wherein $R_f$ is an aliphatic group having from 1 to 20 carbon atoms comprising the steps of (a) providing a partially fluorinated, hydrogen-containing starting material of the formula $$R—O—CF_2CF_2COZ \qquad (2)$$

wherein R is a monovalent hydrogen-containing aliphatic group having from 1 to 20 carbon atoms that may contain one or more oxygen atoms, and Z is selected from —OH, a halogen, a monovalent, hydrogen-containing linear or branched alkyl or alkoxy group containing from 1 to 20 carbon atoms, and an acyloxy radical selected from RCOO— or $ROCF_2CF_2COO$—; and (b) combining the starting material and an unfluorinated coreactant in a suitable vessel;

(c) fluorinating the starting material in the combination from step (b) by direct fluorination; and (d) converting the fluorinated product of step (c) to the perfluorinated acid fluoride.

17. The method of claim 18 wherein the combination of step (b) comprises from at least 10% by weight of the unfluorinated coreactant.

18. The method of claim 17 wherein the unfluorinated coreactant is a low-molecular weight non-chlorinated, non-hydroxylic compound.

19. The method of claim 17 wherein the unfluorinated coreactant is an ether.

20. The method of claim 17 wherein the unfluorinated coreactant is a hydrocarbon ester.

21. The method according to claim 1 wherein the yield of the perfluorinated acid fluoride is at least 50 mole % of the theoretical yield.

22. The method according to claim 16 wherein the yield of the perfluorinated acid fluoride is at least 50 mole % of the theoretical yield.

* * * * *

UNITED STATES PATENT AND TRADEMARK OFFICE
CERTIFICATE OF CORRECTION

PATENT NO.   : 6,482,979 B1
DATED        : November 19, 2002
INVENTOR(S)  : Hintzer et al.

It is certified that error appears in the above-identified patent and that said Letters Patent is hereby corrected as shown below:

Column 5,
Line 12, delete "was 218.9 hr." and insert in place thereof -- was added over 218.9 hr. --
Line 30, delete "CHF2OCF$_2$CF$_2$C(O)F" and insert in place thereof
-- CHF$_2$OCF$_2$CF$_2$C(O)F --

Column 6,
Line 24, delete "P2O$_5$" and insert in place thereof -- P$_2$O$_5$ --

Signed and Sealed this

Seventeenth Day of June, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,482,979 B1
DATED         : November 19, 2002
INVENTOR(S)   : Hintzer, Klaus It is certified that error appears in the above-identified patent and that said Letters Patent is hereby corrected as shown below:

Column 8,
Line 22, delete "of claim 18" and insert in place thereof -- of claim 16 --

Signed and Sealed this

Twenty-fifth Day of January, 2005

JON W. DUDAS
*Director of the United States Patent and Trademark Office*